United States Patent [19]

Thomas

[11] Patent Number: 5,441,681
[45] Date of Patent: * Aug. 15, 1995

[54] PROCESS FOR MANUFACTURE OF CONTAINERS FOR MATERIALS BEING HEATED

[75] Inventor: James E. Thomas, Monroe, N.C.

[73] Assignee: CEM Corporation, Matthews, N.C.

[*] Notice: The portion of the term of this patent subsequent to Oct. 12, 2010 has been disclaimed.

[21] Appl. No.: 130,752

[22] Filed: Oct. 4, 1993

Related U.S. Application Data

[63] Continuation-in-part of Ser. No. 867,891, Apr. 13, 1992, Pat. No. 5,252,274.

[51] Int. Cl.⁶ .............................................. B28B 1/26
[52] U.S. Cl. ......................................... 264/56; 264/60; 264/87
[58] Field of Search ............................... 264/56, 60, 87

[56] References Cited

U.S. PATENT DOCUMENTS 5,252,274  10/1993  Thomas ................................ 264/87

Primary Examiner—Christopher A. Fiorilla
Attorney, Agent, or Firm—Raymond F. Kramer

[57] ABSTRACT

A process for manufacturing containers for holding heated materials includes the steps of depositing a dispersion of fibers in a liquid onto the interior of a liquid permeable female mold, removing liquid from the deposited dispersion by applying a pressure differential across the mold, with the higher pressure being in the interior of the mold, moving a liquid permeable male mold into the female mold, terminating the pressure differential across the female mold, applying a pressure differential across the male mold, with the higher pressure being on the exterior thereof, to press the container onto the male mold exterior, withdrawing the male mold from the female mold, with the container being held to the male mold, and releasing the container from the male mold. In preferred processes the pressure differentials are effected by application of vacuum, the dispersion of fibers is an aqueous dispersion of quartz and/or glass microfibers, with the percentage by weight of the fibers in the dispersion being in the range of 0.2 to 4%, the container is substantially flat cylindrical in shape and is sintered to permanent shape after release from the male mold. A suitable apparatus for practicing such a process is also described, as are containers made with such an apparatus and by such a process. Also described are improved processes and apparatuses in which microperforated and microporous molds are utilized.

8 Claims, 6 Drawing Sheets

PROCESS FOR MANUFACTURE OF CONTAINERS FOR MATERIALS BEING HEATED

This application is a continuation-in-part of U.S. Pat. application Ser. No. 07/867,891, filed on Apr. 13, 1992, now U.S. Pat. No. 5,252,274.

The invention of this application relates to processes and apparatuses that are useful for manufacturing containers for materials being heated. More particularly, it relates to such processes and apparatuses that are utilizable for making said containers from a heat resistant fibrous material, such as microfibrous quartz, which containers are porous, light weight and microwave transmissive, so that the containers and the contents thereof can be heated by microwave radiation and the contents can be ashed, which makes the containers suitable for use in ashing operations that are parts of particular analytical procedures. One aspect of the invention, the employment of microperforated or microporous material in construction of the molds, has applications that are broader than container manufacturing, and processes and apparatuses that utilize or incorporate such mold materials can be employed for molding a wide variety of items from various fibrous materials.

The use of a fibrous quartz supporting pad and a cover of the same material to confine an analytical sample during ashing thereof by means of microwave radiation is described in U.S. Pat. No. 4,565,669 and integrally walled and bottomed containers of microfibrous quartz for use in ashing operations are the subjects of U.S. Pat. Nos. 5,066,843 and 5,378,878. In U.S. patent application Ser. No. 07/662,915, which has been abandoned, there was disclosed an improved process and apparatus for manufacturing containers like those of U.S. Pat. No. 5,066,843. U.S. Pat. No. 2,252,274 describes further improved processes and apparatuses for manufacturing such containers and the present application discloses and claims such an invention in broader terms.

In accordance with the present invention a process for manufacturing containers for holding heated materials comprises the steps of depositing a dispersion of fibers in a liquid onto the interior of a liquid permeable female mold; removing liquid from the deposited dispersion by applying a pressure differential across the mold, with the higher pressure being in the interior thereof; moving a liquid permeable male mold into the female mold; terminating the pressure differential across the female mold; applying a pressure differential across the male mold, with the higher pressure being on the exterior thereof, to press the container onto the male mold; withdrawing the male mold from the female mold with the container being held to the male mold; and releasing the container from the male mold. In preferred processes of the invention the container made is substantially flat or short cylindrical in shape, the dispersion of fibers is a a dispersion of quartz and/or glass fibers or microfibers in an aqueous medium, such as water and at a low concentration therein, the male mold matches the female mold, with the container therein, both the male and female molds are made of microperforated or microporous material (with the microperforated material being more preferred and being of stainless steel), the pressure differentials across the molds are effected by appropriate applications of vacuums to them, the container exterior wall is smoothed by contact with a smoothing element as it is removed from the female mold with the male mold, and the container is sintered to permanent form. Also within the invention of this application are apparatuses for manufacture of the described containers by the described processes and containers made by such processes, as well as processes and apparatuses for molding items from liquid dispersions of fibrous materials, in which the molds are made of microperforated and/or microporous materials. Such mold materials are preferably microperforated, such as that sold by Buckbee-Mears Corporation, of St. Paul, Minn., under the trademark Micro-Perf Screen, and are preferably employed with the microperforations therein being tapered so that the sides of the microperforated materials that are against fibers are of greater diameters than the sides thereof away from the fibers, which facilitates removals of formed items from the molds.

The invention will be readily understood by reference to this specification and the accompanying drawing, in which.

Figure 1:
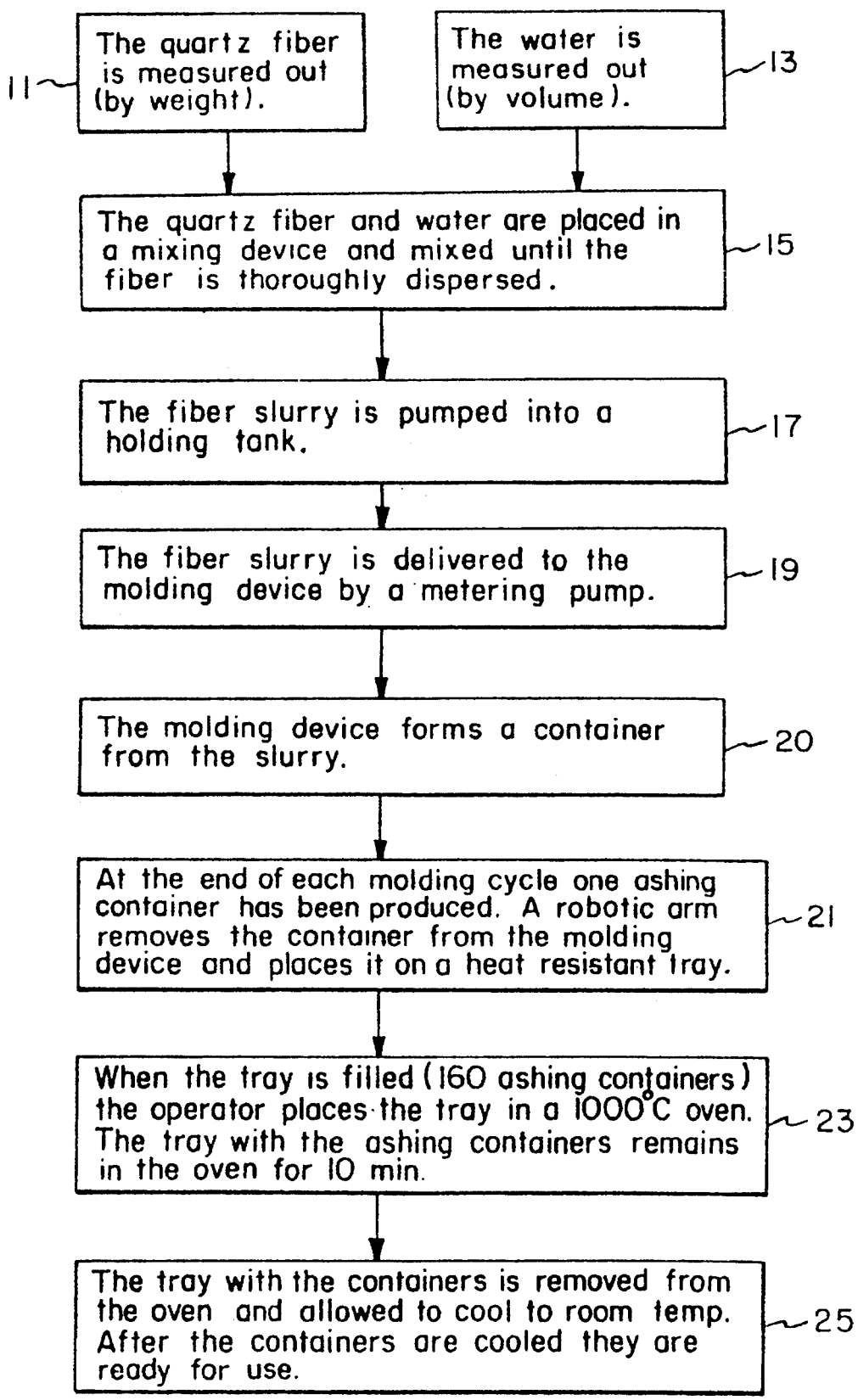
FIG. 1 is a flow diagram of the invented process, illustrating the manufacturing of microfibrous quartz ashing containers for analytical samples.

In FIG. 1 numeral 11 represents the weighing out of the desired amount of quartz microfiber and numeral 13 stands for the measuring out of the corresponding amount of water, to make a dilute dispersion of the fibers in the water. The quartz microfibers and water are mixed in a suitable mixer, which step is represented by 15, after which the slurry made is pumped (17) into a holding tank, where it is held ready for delivery to the molding apparatus. When molding is to begin the fiber slurry is metered (19) by a metering pump to the molding apparatus (actually to the female mold thereof). Numeral 20 identifies the molding operation, the various steps of which will be described in detail later, This step and steps 17, 19 and 21 may all be under microprocessor control whereas the other steps are normally under human control (although they too, can be automatic, as by being under microprocessor control). After the "green" container form has been produced a robotic arm removes it from the molding apparatus and deposits it on a heat resistant tray (operation 21), When the tray is full with the desired number of green container forms it is placed in a 1,000° C. oven, where it remains for a sufficient time, e.g., about ten minutes, so the containers are sintered or cured to form retaining state (operation 23). In a final operation 25 the tray of containers is removed from the oven and allowed to cool to room temperature, after which the containers are ready for use.

Figure 2:
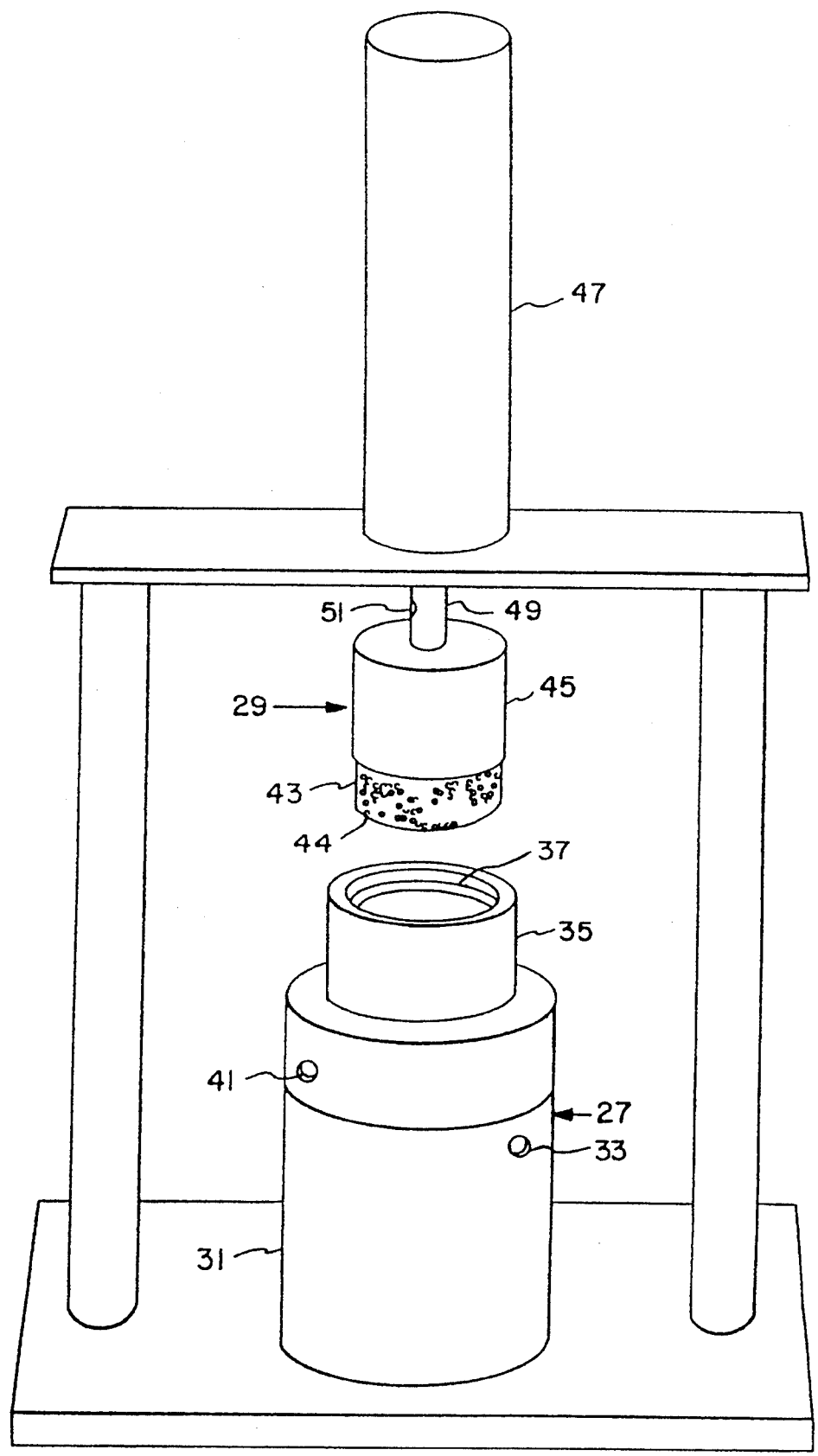
FIG. 2 is a three dimensional view of the apparatus of this invention.
Figure 3:
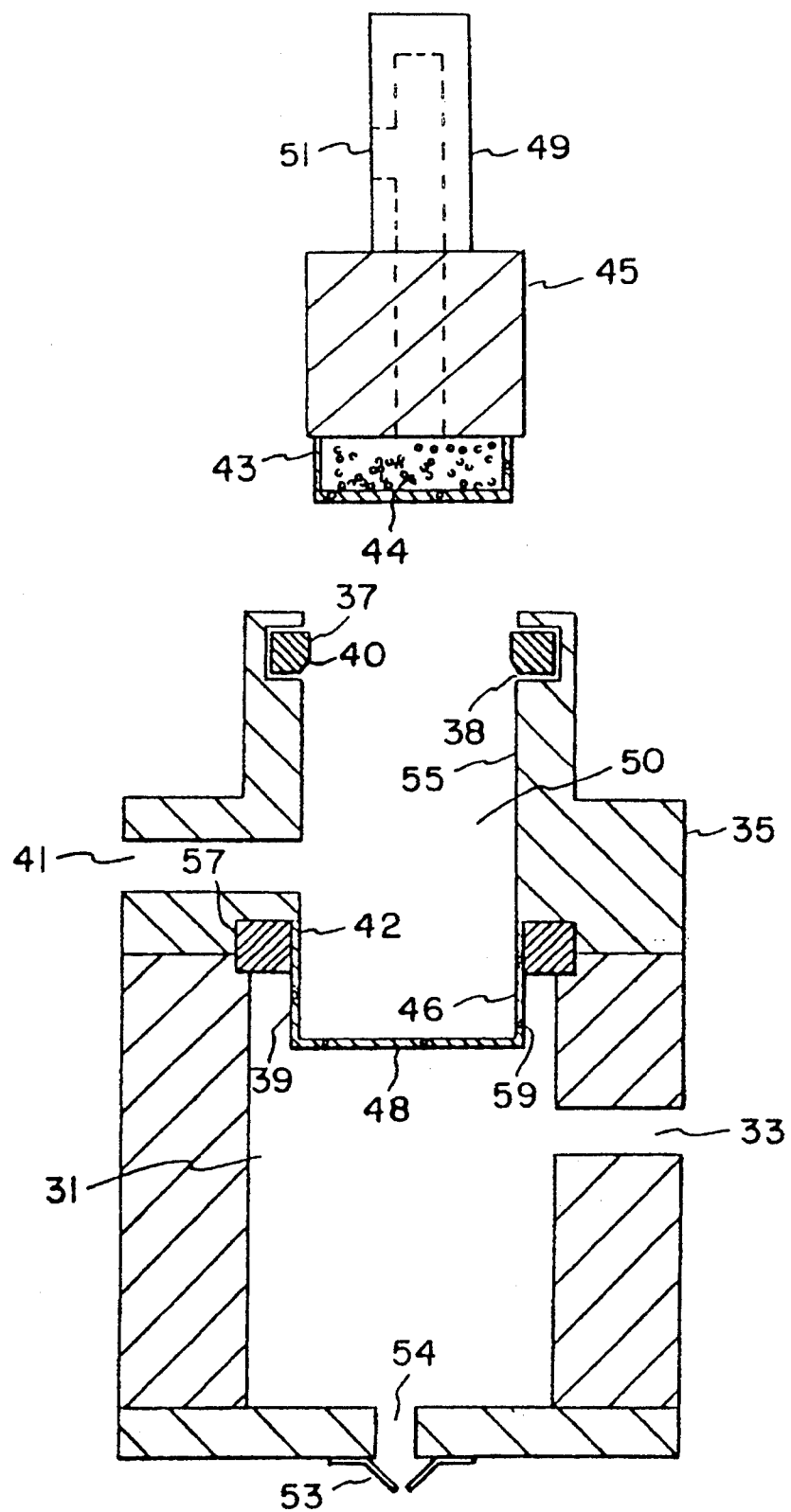
FIG. 3 is a sectional elevational view of the operative apparatus of FIG. 2, without supporting elements.
Figure 4:
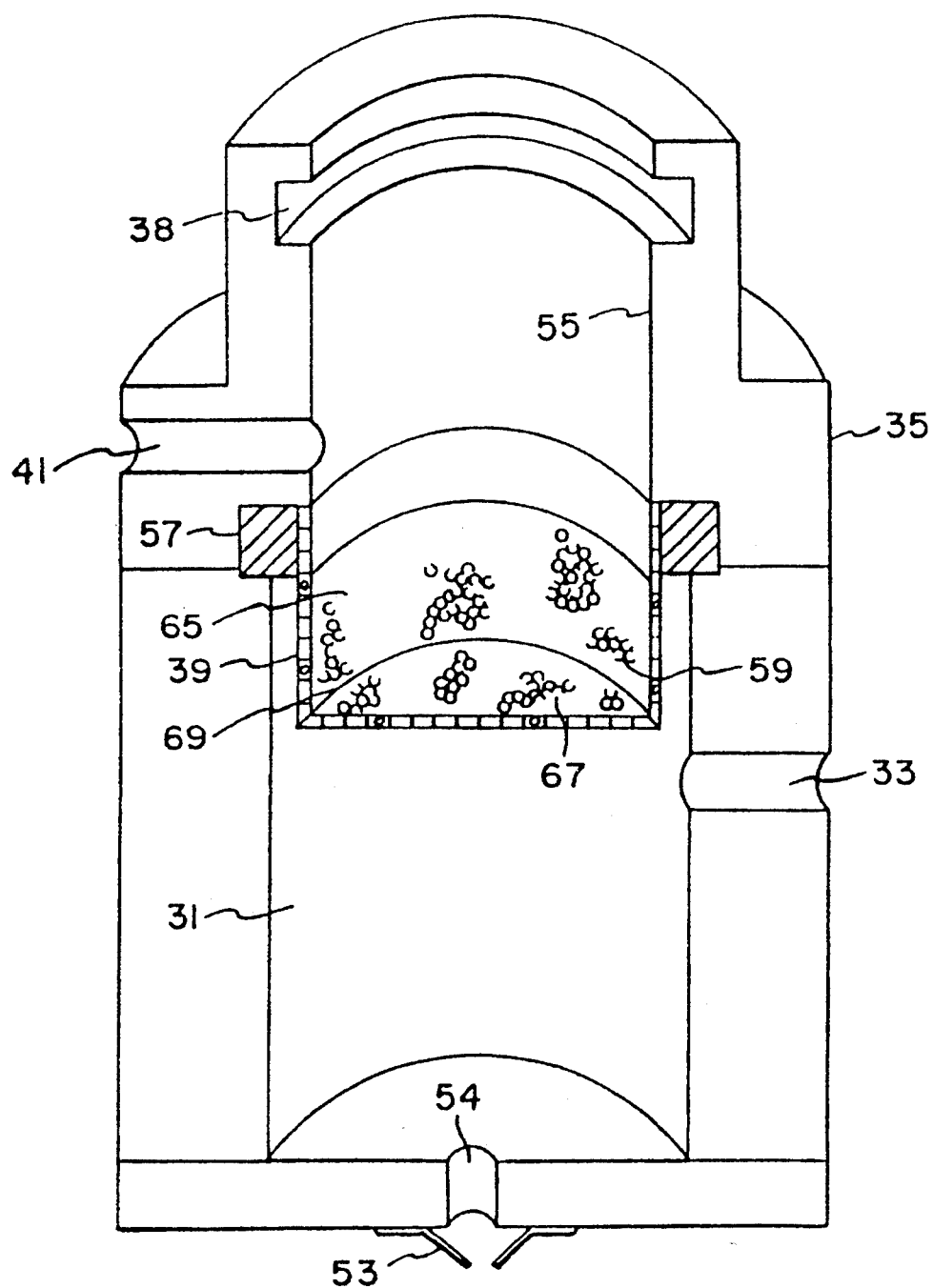
FIG. 4 is a cutaway perspective of the female mold, vacuum chamber and smoothing assembly portion of the molding apparatus.

In FIG. 2, 27 designates a female mold assembly portion and 29 identifies a male mold assembly portion of the invented molding apparatus. Vacuum/pressure chamber 31 is located at the lower part of female mold assembly portion 27 and is communicated with either a vacuum source or a pressure source through port 33. Cylinder 35 is located at an upper portion of female mold assembly portion 27 and inside the cylinder is a smoothing form (ring) held in groove 38 (see FIG. 2). Before the smoothing ring and above most of the chamber 31 is the female mold but such does not show in FIG. 2 although it is illustrated in FIGS. 3 and 4, as 39. Fiber slurry inlet port 41 delivers the slurry above vacuum/pressure chamber 31 and to the interior of female mold 39, onto which interior the fibers are deposited. The male mold assembly portion 29 includes microperforated male mold 43 which is mounted on an appropriate hollow support 45 which is connected to a double acting pneumatic cylinder/piston 47 through hollow connector 49 so that male mold 43 may be moved either downwardly or upwardly, with the downward motion being to finish the container interior and the upward motion being to detach the container from the female mold and smooth the exterior thereof as the container is removed from the female mold. The microperforations of the male mold are represented by numeral 44, and will be described in detail later. Vacuum/pressure port 51 connects the interior of the male mold with sources of vacuum or pressure, as desired. The various supports for the apparatus portions are indicated schematically and need not be separately described because their supporting functions are self-evident from FIG. 2.

FIG. 3 illustrates much the same apparatus as is shown in FIG. 2 but omits the supports and the means 47 for moving the male mold down and up, as desired. However, it does show details of the female mold 39, the vacuum/pressure chamber 31 and check valve 53, at the bottom of the vacuum/pressure chamber 31. To avoid unnecessary repetition only a few parts of the apparatus illustrated in FIG. 3 will now be described. Smoothing ring 37 fits in matching groove 38 and extends beyond cylinder internal wall 55 a sufficient distance so as to smooth the exterior of the green container as it is removed from the female mold with the male mold and passes through the smoothing ring. The positioning of the female mold is shown, with it being held in place by collar 57. Female mold 39 includes wall 46 and bottom 48 portions and the microperforations of such are represented by numeral 59. Check or one-way valve 53, at the bottom of vacuum/pressure chamber 31, helps to maintain vacuum in the chamber, when that is desired, and holds the liquid (water) from the slurry in chamber 31 until it is ready for discharge through drain 54 (in the bottom of chamber 31), which can be effected by releasing the vacuum or by placing the chamber under pressure. The discharged liquid can be recycled and any small proportion of fibers that may be in it can thereby be recovered.

Figure 5:
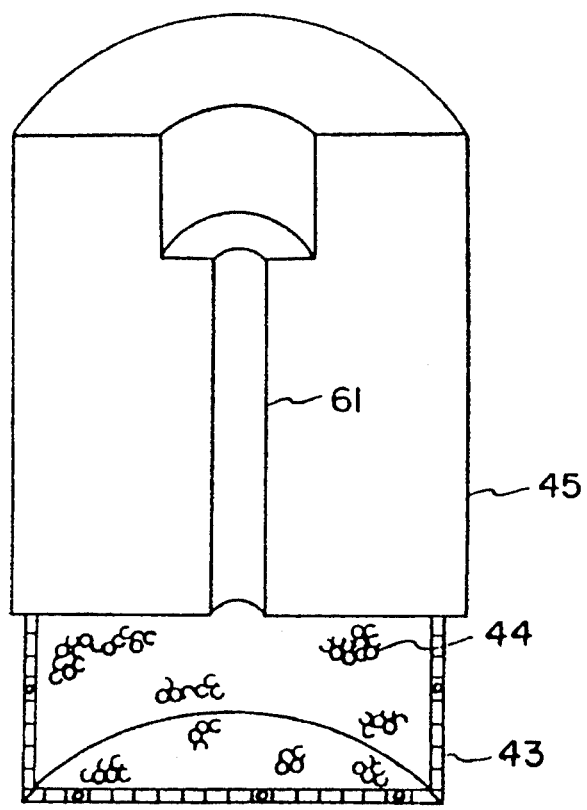
FIG. 5 is a cutaway perspective of the male mold and piston assembly portion of the molding apparatus.

In FIG. 5 there is illustrated male mold 43 held to piston-shaped support 45, which includes an internal passageway, 61 for transmission of vacuum or pressure to the volume inside male mold 43. In microperforated screen 43 the microperforations, only some of which are shown, are represented by numeral 44.

Figure 6:
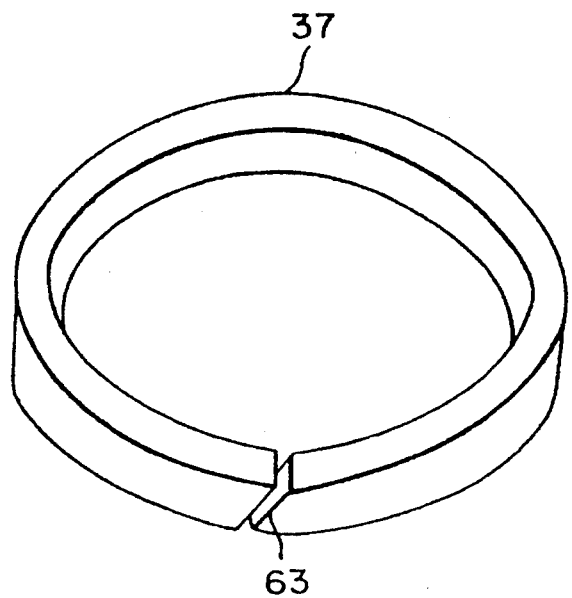
FIG. 6 is a perspective view of the smoothing ring.

FIG. 6 shows the form of the smoothing ring, which is preferably of a synthetic organic polymeric plastic, e.g., polyfluoroethylene (Teflon ®). The ring is preferably circular, shown, but other shapes can also be employed, to match the wall shape of the container made. Smoothing ring 37 is in the form of a flat cylinder which is held in place in groove 38. As illustrated, ring 37 is split at an angle 63 to facilitate insertion into the groove 38 and the ring size, when in the groove, is such as to press against the exterior wall of the green container as it removed from the female mold. The smoothing ring is desirably flared or tapered at the bottom 40 thereof so as to promote entrance into the ring of the green container without peeling back of the upper lip 42 thereof.

FIG. 4 is much like the female mold portion of FIG. 3, with the smoothing ring removed, so it requires little further description. However, it will be mentioned that the microperforated female mold thereof includes integral wall and bottom portions 65 and 67, respectively, which are welded together at seam line 69.

Figure 7:
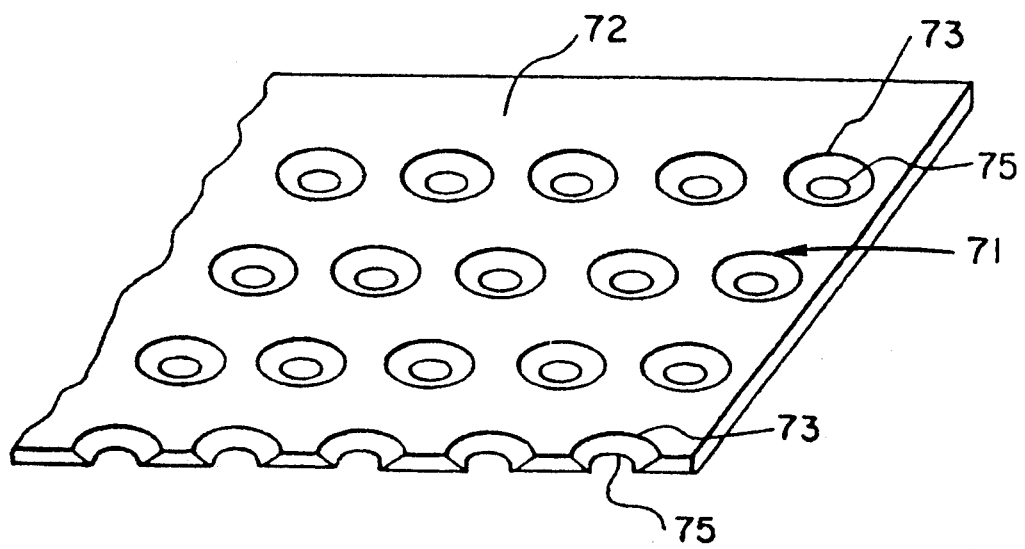
FIG. 7 is a magnified schematic view of a small piece of microperforated material, illustrating tapered passageways through such material.

In FIG. 7 there is shown a representation of a microperforated material of a type like that used to make the molds of this invention, especially the female mold. As illustrated, the perforations 71 are of greater areas (and diameters) on the upper face of sheet 72 than on the lower face thereof. The differences in diameters is exaggerated in the drawing and the orientation of the microperforations may be different from that employed in making the molds of the invention but FIG. 7 is intended to show the tapered nature of the microperforations, with, the larger portions thereof 73 being on the face of the mold in contact with the green container and the smaller portions thereof 75 being away from the container.

The containers that are made by the invented processes and with the invented apparatuses may be of any of various shapes, including tapered walled, cylindrical and/tubular (of other than circular cross-section), but are preferably of essentially flat cylindrical shape. They will normally have flat bottoms which are integrally formed with, the side wall or walks. The containers are preferably made from microfibrous quartz (for ashing containers that are subjected to high temperatures, such as 500° C. or even higher) but sometimes they may be made of thicker quartz fibers. Glass microfibers or fibers may be employed when the containers are to be subjected to lower temperatures, as when materials are to be heated to lower temperatures than ashing temperatures, but even in such cases borosilicate glasses are usually preferred.

The containers made will normally be of substantially uniform wall and bottom thickness, with such thickness normally being in the range of 0.2 to 5 mm., preferably 0.3 to 4 mm., and more preferably 0.2 to 0.3 mm. Such a container will usually measure 2 to 10 cm. in diameter, preferably 4 to 6 cm., and will be 1 to 2 cm. high, e.g., 4.7 cm. in diameter and 1.5 cm. high. The ratio of height to diameter (or to major horizontal dimension) will normally be less than 1:1 and preferably will be no more than 1:2. A preferred such ratio will be in the range of 1:2 to 1:10, preferably 1:2 to 1:5, e.g., about 1:3. The density of the wall and bottom material, in grams per square meter of one surface (considering the container to be laid out in a plane, like a pattern will usually be in the range of 50 to 500, preferably 100 to 300 (corresponding to 0.02 to 25 and 0.04 to 0.15 g./cc., respectively). In addition to being light in weight the container will be porous, so as to absorb and distribute any liquids of low viscosity and low surface tension over the interior surfaces thereof, which, for ashing containers, facilitates even evaporation, combustion and ashing and promotes air movement through the container walls, which facilitates oxidation and ashing. Porosity may be measured by recording the pressure drop across the container wall at a certain air velocity and good porosity is recorded when the pressure drop is in the range of 0 to 10, of mercury at an air velocity of about 1 cm./second, such as 3 mm. of mercury through a 2 mm. wall and 6 mm. of mercury through a 3 mm. wall.

Similar pressure drops are sometimes also obtainable when the air velocity is increased to 5 or 10 cm./sec., which is indicative of further improved air permeability (or porosity).

Although the desired characteristics of ashing and heating containers for analytical uses are described above it is evident that the invention has application to making such types of containers of different thicknesses, porosities, densities, shapes and materials.

The preferred ashing containers are of microfibrous quartz. The microfibrous quartz is normally of a diameter in the micron range, which range may be 0.1 to 10 microns, preferably 0.3 to 5.5 microns and more preferably 0.5 to 1 micron, e,g., of a nominal diameter of 0.65 or about 0.65 micron. Such quartz microfibers are available from Manville Sales Corporation, Toledo, Ohio and are described in a bulletin issued by such corporation, which is entitled Tempstran ® Glass Micro-fiber, and is dated Apr. 1, 1989. The bulletin is directed primarily to glass microfibers but corresponding quartz microfibers are also available from such corporation, with the glass codes being modified by addition of a suffix Q to indicate that the microfibers are of quartz instead of glass. While any of the quartz microfibers described in the bulletin may be employed, it is preferred to utilize that identified by the designator 106-Q, which is of a nominal diameter of 0.65 micron. In some cases a mixture of quartz and borosilicate glass fibers will be preferable, with the borosilicate being a minor proportion of such mixture, such as from 5 to 20%, e.g., about 10%. Other glasses than borosilicate may also be employed, but most such are not as good in resisting heat damage, so the borosilicate glasses will usually be preferred. Although microfibrous quartz and glass are preferred starting materials, the invention also has applications to the forming of containers from quartz and glass fibers of greater diameters, such as up to a millimeter or so. For higher temperature heatings and ashings quartz microfibers are preferred but for lower temperature applications borosilicate glasses and other glasses may be employed, depending on the glass characteristics and the particular applications. Also, for applications wherein heat resistance is irrelevant, such as for manufacturing extraction thimbles, ordinary glass fibers, cellulose, plastic or other fibers, preferably microfibers, may be utilized. Of course, plastics may be joined or cured by application of less heat than quartz or glass, and cellulosic fibers will not be sintered (containers made from them may be used in "green" form).

The dilute suspension of quartz and/or glass (or other) fibers may be in any suitable liquid medium, including ethanol, isopropanol, kerosene, ethylene glycol and other organic liquids but it is preferred to employ aqueous media instead, such as aqueous isopropanol or water, with water being the most preferred medium. The "concentration" of the fibers in the medium will normally be in the range of 0.1 to 10% (all percentages given in this specification are by weight, unless otherwise indicated), preferably 0.2 to 4% and most preferably 0.3 to 2%, e.g., about 0.4%. The temperature of the slurry, dispersion or suspension of fibers in the medium will normally be about room temperature, within a range of 10° to 35° C., usually 20° to 30° C., such as about 25° C. A wetting agent or a dispersing agent, such as sodium lauryl sulfate or potassium xylene sulfonate, may be present in the medium to promote dispersion of the fibers and in some cases, to promote a more even deposition of the fibers on the female mold. An anti-foaming agent, such as a silicone fluid, e.g., dimethyl silicone, may be employed to prevent excessive foaming of the dispersion due to the content of wetting agent or hydrotrope. In some instances a gum such as sodium alginate or sodium carboxymethyl cellulose, may also be present to promote adherence of the fibers to each other but care must be taken that the gum does not block the female mold openings. Although such additives to the dispersion may be useful they are usually not required and often any such materials will be omitted from the dispersion because they can cause ashing or calculation problems if some remains in the container after sintering or curing.

The mold may be made of any of various suitable materials that are pervious to liquids and which will not allow the fibers employed to pass through them to an objectionable extent. Thus, sintered metal or sintered glass, porous plastic or screening can be employed in some processes but the first three tend to plug up during use and are difficult to clean, and screening does not release the molded items as well as microperforated metal, which works best, being repeatedly usable without plugging, being easy to clean and releasing well. Normally, in the making of the invented containers the proportion of fibers passing through the female mold openings will be less than 5%, preferably being less than 3% and more preferably being less than 2%, e.g., 0.5 to 1%. Any such fibers will preferably be recycled, as will be the medium, so ultimately all the fibers will be utilized. To minimize passage of the fibers through the mold openings such openings will desirably be less than the lengths of the fibers and even will be less than the fiber diameters when that is possible. However, when microfibers are employed that may not be feasible so in such cases the fiber lengths should be such that the fibers do not readily pass through the mold openings when they are oriented parallel to the mold surface. In some such cases it may be desirable for the fiber lengths to be high multiples (even hundreds) of the diameters, although it has been found that due to the matting effects accompanying depositing of many fibers at a time it is not always important to have the fiber lengths much greater than the female mold openings.

While it is possible to utilize screening for the molds of this invention, it has often been found that fibers yore readily adhere to such screening (becoming entangled in the woven screening) than to perforated plate or sheet materials of construction for the molds, especially for the female mold. Preferred such materials have been characterized as microperforated but the openings therein are usually significantly larger than micron size. Suitable opening sizes for the microperforated materials may be in the range of 50 microns to 1 mm., preferably 100 to 700 microns and more preferably 200 to 600 microns. While the openings may be uniform through the thickness of the material they will preferably be tapered, with the smaller opening being ¼ to 9/10 the diameter (or other major measurements), if other shaped openings are used) of the larger opening. Preferably the smaller openings will be circular, as will be the larger openings, and the smaller ones will be ⅓ to ⅔ of the diameter of the larger ones. The microperforated material will normally have from 10 to 60% of its surface perforated and preferably the openings will be 20 to 40% of the surface on the larger opening side and 10 to 30% of the surface on the smaller opening side. The thickness of the material is not critical so long as it is formable or moldable to mold shape but usually it will be in the 200 micron to 1 mm. range. Various materials may be used for the microperforated molds, including synthetic organic plastics, such as polyacetals, polyacrylates, polystyrenes, nylons, and phenol formaldehydes, but it is preferred to employ metals and metal alloys, such as aluminum, stainless steel and Monel metal, of which stainless steel is preferred. Such material is form retaining in thin sheets and parts and yet is formable and may be welded or otherwise joined to form the desired molds. A preferred microperforated stainless steel sheet material from which the present molds may be made is available from Buckbee-Mears Corporation, St. Paul, Minn. under the name Micro-Perf Screen. It is of 304 stainless steel, of a half hard temper, 380 microns thick, of a hole size (diameter) of 460 microns (for the smaller openings), a pitch of 0.031 and an orientation of the holes of 60°. The open area or hole area is 31% of the surface of the side with the smaller openings. Such a sheet, while not transparent, can be seen through, and it has been employed as microwave and TV shields. Such materials may be made by a photoetching process which results in the tapered holes mentioned, with the hole distribution matching a pattern of openings in a mask that was used in the photoetching process. Photoetching or equivalent perforating process may be carried out on the sheet material or on the finished mold shape formed from unperforated material and the molds may then be photoetched and thereby perforated.

It has been found by experimentation that when the microperforated metal mold surface with the larger sized openings faces the material being molded (the container), the container releases more easily from the mold (female or male), less snagging of fibers occurs and the container wall released is smoother, which are significant advantages. Containers are moldable from microperforated metal molds wherein the mold surfaces, facing the molded item include the smaller openings but the container surface quality is not as good.

The smoothing ring of the apparatus may be made of any suitable material that is capable of smoothing the exterior wall of the green container, as it is withdrawn from the female mold. Suitable such materials include metals and alloys, such as copper, tin plated steel, stainless steel and brass, and plastics, such as polypropylene, nylon and polyfluoroethylene (PFE) or polytetrafluoroethylene (PTFE of Teflon ®). Of these the polyfluorinated ethylenes are much preferred because they, are sufficiently hard, and loose fibers do not adhere to them readily.

The other parts of the apparatus may be made of conventional materials of construction, such as steel, stainless steel, enamelled steel, aluminum, brass, copper, iron, plastics, synthetic rubber and wood, and the choices of such materials will be apparent to one of skill in the art.

In the process of this invention the dilute dispersion of fibrous material for the container is made by mixing the fibers with a suitable medium, such as water, in an appropriate mixer. For small scale operations such mixing may be of single container charges of fibers, so that only enough dispersion is made as will produce a single green container. For production runs it has been found convenient to employ a 55 gallon (208.2 liters) drum as the mixing container, with the mixer used being of the Lightnin' ® type, or equivalent which is adjustably clampable to the drum lip. The dispersion may then be transferred to a holding container for subsequent delivery to the female mold.

The dispersion of fibers is fed to the female mold in the amount needed to deposit the desired container, of the desired wall and bottom thickness. Usually a metering pump will be employed that controllably delivers the correct volume of dispersion to the mold. Passage of the liquid medium through the mold openings is facilitated by a pressure difference, preferably a vacuum, and such difference will normally be in the range of 150 to 750 mm. of mercury. While the liquid medium passes through the female mold openings from interior to exterior thereof, the fibers (except for a small proportion thereof) do not, and instead they deposit on the mold inner wall, forming a uniformly thick container thereon, with the container exterior being in contact with the mold interior.

After depositing of the fibers on the female mold wall and bottom and the removal of the liquid medium from contact with the fibers because it drains into a receiver below, the fibers are found to be satisfactorily interlocked, in non-woven matted form, so that the container resulting upon removal from the mold is form retaining when free standing. However, although the container exterior is readily removable from the mold interior and is fairly smooth walled when the mold exterior is smooth walled, some fibers may project from it. Additionally, the container interior, not having been pressed against any smooth surface, may be somewhat ragged. The smoothing of the container interior is effected by moving into the interior of the container (and the female mold) a male mold that conforms to the female mold, allowing for the thickness of the molded container. Such male mold is moved into position inside the female mold by any suitable reciprocatable mechanism, such, as a double acting pneumatic piston/cylinder combination. This mechanism has sufficient stroke to be capable of inserting the male mold to the bottom of the female mold and of raising it a sufficient clearance distance above the female mold. After the male mold has been inserted into the container the pressure differential (vacuum) applied to the female mold to hold the fibers to its interior is terminated and a similar differential, about 150 to 750 mm. of mercury, and preferably a vacuum, is applied to the male mold to draw the container interior against the male mold exterior, thereby smoothing the interior container wall and bottom.

While still maintaining the pressure differential that holds the container to the male mold such mold and the container are withdrawn from the female mold by, a withdrawal action of the pneumatic means and in such withdrawal the container outer is smoothed by contact with the smoothing member, previously described. Such smoothing action, in conjunction with the pressure differential, causes any projecting fibers to be flattened against and incorporated into the container wall, thereby obviating any hitherto desirable trimming step. The smoothing ring or smoothing member of other suitable shape to match the container geometry is preferably flared enough where the leading edge or lip of the container first enters it so that the container will be guided into position and will not have the lip portion abutting the smoothing element bottom, which could result in flattening, mashing or accordion pleating of the container. Normally, such flaring will not extend beyond the first half of the smoothing ring height (in the direction of travel of the container).

After the finished green container has been removed from the female mold, in smooth walled form, it is released from the male mold by termination of the previous pressure differential (lower pressure on the male mold interior and by application of a higher pressure to the mold interior. The container drops onto a heat resistant tray held by an operator or alternatively, in more mechanized operations, the container is removed by robotic arm and is placed on a heat resistant tray.

The individual green containers are sufficiently form retaining so that they can be gently moved from place to place without collapsing, but to be really form retaining under use conditions they should be heated to a substantially elevated temperature, at which the fibers fasten together (or are sintered). Such sintering operations are conducted in ovens that are capable of heating the containers to sintering or fastening temperatures. For plastic containers, made from thermoplastic fibers, such temperatures may be in the range of 200° to 400° C. whereas for glass containers they may be in the range of 600° to 1,000° C. and for quartz containers the temperatures may be in the range of 800° to 1,200° C., usually about 1,000° C. Of course, plastic containers, the fibers of which fasten together (and release) at 200° C. would not be useful as ashing containers but could be employed as extraction thimbles, as could containers made of cellulosic fibers. After cooling to room temperature or thereabout the finished container(s) can be removed from the oven and may be employed for such operations for which it/they is/are suitable, depending in large part on its/ their resistance to elevated temperature exposure.

In the above description of the invented process the various steps recited are given in preferred order but it should be understood that in some instances such order may be changed, with the process still being within the invention. For example, the pressure differential may be applied to the male mold before the pressure differential across the female mold wall and bottom is terminated. Similarly, although the apparatus illustrated and described is vertically oriented it may be disposed at other operative angles. The female mold described is stationary but it may be rotating about its axis or may be otherwise moving, sometimes to promote better deposition of fibers on the mold interior surfaces. Also, between the removal of the container from the male mold and the sintering operation there may be interposed an intermediate drying step, if that is considered to be desirable under the particular circumstances.

The apparatus has already, been described in the drawing explanation, and it is such as to he useful in carrying out the processes described above. However, additional details about the apparatuses will now be given. The female and male molding means may each be made of single pieces of screening or perforated material or bottom and wall portions thereof may be suitably joined together to form such molds or shaping means. Screen molds may be formed to shape, as may be perforated metal molds. Plastic molds may be molded to shape and microperforations may then be made in them by the photochemical method previously described. Microperforated metal or alloy molds may be formed first to shape and then microperforated too, by the same type of process. Alternatively, the microperforated molds may be made from microperforated sheet material, preferably stainless steel, by forming it into a flat cylinder and a circular bottom and welding such parts together. Microperforated plastic sheet, preferably made from a thermoplastic, may be made in essentially the same manner but instead of welding the parts together they may be heat or solvent fused. The preferred stainless steel microperforated molds are sufficiently strong to he for retaining during the molding process, while at the same time presenting, a smooth surface to the container surface in contact therewith. Also, due to the tapered nature of the perforations therein, the mold readily releases the formed green container from it when desired, without snagging fibers from such container. During the molding operation it has been noted that the microperforations, do not plug up objectionably, which would interfere with the even depositing of the fibers to form the container.

While the means for delivering the desired amount of dilute fiber dispersion to the female mold (or to a holding vessel from which such may subsequently, be fed to the mold) is preferably a metering pump, such amount may be hand measured or weighed, by weighing means, to ensure that the desired amount of fibers is converted to container shape. The pressure differentials applied to the molds and to other parts of the described apparatus, such as the vacuum/pressure chamber and the male piston (to release the green container from it) can, in appropriate circumstances, be vacuum or pressure. Kith respect to the invented female molds vacuum is preferably employed to draw the liquid dispersion of fibers to the mold interior to deposit the fibers thereon and pass the liquid medium through the perforations but in suitable circumstances pressure could be applied to the dispersion to accomplish the same result. In similar fashion external pressure applied to the system could promote release of the container from the female mold and holding of it oh the male mold, as such is moved upwardly but it is decidedly more convenient for vacuum to be applied internally of the male mold to hold the container to it. The means for applying pressure to the vacuum/pressure chamber to drive the contained liquid (and any fibers present) out may be replaced by a source of vacuum externally connected to draw the contents out through the check valve, although the described pressure operation is more convenient. Similarly, in other parts of the apparatus vacuum means may be replaced by pressure means suitably located and vice versa.

The removed liquid medium and any fibers present therein may be collected in a sump below check valve 53 and from there it may be recirculated through the system, with allowance being made for its content of fibers when making up the fibrous medium to be charged to the female mold. Such recycling is desirable both to conserve the fibers and to avoid disposal problems.

The means for moving the male mold vertically, a double acting pneumatic piston, may be replaced by other up and down movements, such as hydraulic means and conventional mechanical means, and similar replacements as will occur to one of skill in the art may be effected with respect to other elements of the described apparatus.

Although the process described cam be carried out with the aid of the described apparatus by manual means it is often preferred that the operations be at least partially automatic and that automatic operation is preferably microprocessor controlled. Thus, steps 19, 20 and 21 of FIG. 1 may be microprocessor controlled but it is also possible to utilize such control for steps 11, 13, 15 and 17, and even for steps 23 and 25. While microprocessor control is preferred other electronic and mechanical control mechanisms may be substituted for it in whole or in part.

The apparatus has been illustrated to produce a single container at a time (with the exception that a plurality of containers is sintered together) but the apparatus may be modified, as by inclusion of a plurality of molds (female and male) to produce a plurality of containers at a time. Such operations will be more efficient than single container production because a single source of liquid medium containing dispersed fibers may be employed, as may be single sources of vacuum and pressure, and a single sump for collection of liquid medium to be recycled. Also, production capacity can be increased significantly and labor and supervision can be reduced per unit made.

The major advantages of the present invention over the closest prior art known to applicants have already been alluded to but such advantages and some of less importance will now be recounted. Because the preferred apparatuses and processes may be automated (whereas the previous apparatuses and processes were primarily manual) manufacturing costs are decreased and production rates can be increased significantly. The employment of microperforated molds, especially those with larger openings thereof facing the container side, produces-containers that are smooth surfaced, without trimmings of projecting fibers being required. The use of a smoothing element or ring additionally smooth the exteriors of the containers made. Due to the evenly distributed microperforations the flow of liquid medium through them is even, so that the fibers are evenly deposited on the mold and a uniform integrally walled and bottomed light weight and porous container results. Such green containers are more readily uniformly sintered and often are stronger, allowing repeated uses as heating or ashing containers (or as extracting thimbles or for other purposes).

The following examples illustrate but do not limit this, invention. Unless otherwise indicated all parts in these examples, this specification and the claims are by weight and all temperatures are in degrees Centigrade.

EXAMPLE 1

A 0.4% dispersion of microfibrous quartz (Manville Tempstran ® 106-Q, which is of a nominal microfiber diameter of 0.65 micron), in room temperature (25° C.) water is made by mixing together in a blender 0.8 gram of the microfibrous quartz and 200 ml. of water. After three minutes of blending at medium speed the dispersion is satisfactorily mixed and is in fluid form and ready for addition to the molding apparatus. The apparatus employed is that described in the foregoing portion of this specification and in the description of the drawing, and in this embodiment of the invention is equipped to make only one green container at a time, although a plurality of containers may be sintered together.

A vacuum of about 300 mm. of mercury is drawn on the chamber 31 through port 13 and the dispersion is fed to female mold 39 through inlet port 41. When a larger batch of dispersion is made, from which a plurality of ashing containers may be manufactured, a metering pump will desirably be employed to measure out the 200 ml. charges to the female mold for each container to be made but in the present case such is not employed (although it could be). The dispersion is fed to the mold in such manner that it fills the mold and most of the volume of the cylinder 50, so that as the liquid is drawn through the microperforated wall and bottom of the female mold a substantially even wall and bottom thickness is obtained. The female mold is made of microperforated 304 stainless steel of the type previously described in this specification, which is obtained from Buckbee-Mears Corporation, St. Paul, Minn., and which is supplied under the name Micro-Perf Screen. Such screen is welded into a flat tube for the side wall thereof and is cut to a disc for the bottom, and such parts are welded together to form the female mold, which is about 4.7 cm. in diameter and about 1.5 high, so that it is suitable for making a container that is about 0.25 thick, 4.7 mm. in diameter and 1.5 cm. high. In some instances the flat container may be somewhat tapered but usually the taper will not exceed 5° or 10° from the vertical, with the container being open mouthed. After deposition of the green container on the female mold, which takes about 5 to 8 seconds, depending on the vacuum employed or other pressure differential, the container will have been finished only on the exterior thereof, and surfaces in contact with the smooth mold wall. The next step in the molding operation is for the male mold, which is made to conform to the female mold, allowing for the thickness of the container material, to be lowered into place inside the female mold by actuation of the pneumatic piston/cylinder combination with pressurized air. The male mold is lowered far enough so as to press the container bottom against the female mold bottom, thereby smoothing the inside wall(s) and bottom of the container, which operation takes about 1 to 30 seconds, e.g., about 2 seconds, after which the vacuum to the female mold is discontinued and a similar vacuum is applied to the interior of the male mold and that mold is withdrawn from the female mold, being raised upwardly, taking the container with it. As the container passes the PTFE (Teflon ®) smoothing ring, which is tapered on the bottom portion thereof sufficiently so as to facilitate passage of the container edge into the ring without it being mashed or "accordioned", the ring further smooths the outer wall of the container by contact with it, pressing back into the container wall any fibers that might have been projecting from such wall, due to having been adhered to the female mold wall. When the container is in its highest position the vacuum is discontinued and a suitable pressure, which may be about 1 kg./sq. cm. is applied to the male mold interior, which releases the container from the mold. The vacuum chamber is then pressurized to drive the liquid in it out through the check valve and the liquid is collected, to be reused to make an additional dilute fiber dispersion. The released container is then placed in a sintering oven, which is at a temperature of 1,000° C. and is heated therein for ten minutes, after which the microfibers are found to be held together permanently. The container made is light weight and porous, allowing air to pass through it during ashing operations, and it is resistant to the heat of ashing, which is usually above 500° C. and sometimes can be as much as, 800° C. or 1,000° C. The containers made are of a wall and bottom thickness of about 0.25 mm., a diameter of about 4.7 cm. (internal, at the top and a height of about 1.5 cm. (internal), which is a convenient size for use as a container for analytical samples to be ashed by microwave ashing processes. The porous, nature of the container makes it especially useful for employment in ashing processes wherein a flammable solvent is present which has to be burnt off during the initial part of the ashing process, because such, a porous container promotes smoother burning of the solvent and minimize "bumping" or flaring which could cause the loss of sample. It has been found that the containers made can be used for multiple ashings, with as many as fifty being possible in many cases.

EXAMPLE 2

The procedure of Example 1, described above, is one in which operations are largely manual and only a single container is made, and such was so described as an example of a simple form of the invention. However, in production runs such labor intensive processes are costly and therefore it is preferred that the various operations be automatic, as described herein. In a preferred automatic process the operations of the apparatus are controlled by a microprocessor which initiates the weighing and transporting of the microfibers and the metering of the water to the mixer or blender, controls the mixing and meters the desired quantity of dispersion to the female mold, and applies vacuum or other pressure differential to the female mold to draw the aqueous medium through the mold and deposit the fibers on the mold interior. Next the vacuum chamber is automatically pressurized to discharge liquid medium from it through the check valve to a sump, from which it can be recycled to make additional dilute fiber dispersion. By means of microprocessor control the male mold is then lowered into place inside the female mold and is placed under vacuum, which draws the green container to it from the female mold, after which the male mold is raised, with the container on it, and the container is discharged from the mold by application of pressure to the male mold interior. A robotic arm transfers the green container to a heat resistant support, which is then automatically or manually inserted into a sintering oven and the container is subjected to the sintering treatment described in Example 1. Alternatively, the support may hold a plurality of green containers to be sintered, such as 10 to 200, e.g., 160, and all may be sintered at the same time, using one heating oven. All the described operations from the weighings and measurings of dilute components to the removal of the green containers from the male mold are microprocessor controlled in the example given herein but in some instances only the steps from metering the dilute fiber dispersion through the transfer of the green container from the male mold to the heating tray are so controlled. The resulting containers are like those described in Example 1 and have the desirable use properties described for those containers. Because the microprocessor controlled operations proceed quickly and occur simultaneously or partly simultaneously the operation, after mixing of the dispersion up to sintering, can take as little as 10 or 15 seconds and rarely will require more than a minute, from depositing the fibers on the female mold to removing the green container from the male mold.

EXAMPLE 3

In this example a plurality of heatable containers is made at a time, using borosilicate glass microfibers instead of quartz microfibers, with the microfiber dimensions being the same. In another embodiment of the invention the microfibers are 90% quartz and 10% borosilicate glass. Instead of feeding only one female mold at a time the metering pump feeds as many as ten such molds from a common source of a dilute dispersion of the microfibers. Similarly, a common source of vacuum is employed for all the female molds and a common vacuum chamber is pressurized by a single pressure source and the liquid medium from all the molds is collected together and recycled to the mixer in which the new dilute dispersion is to be made. The male molds are moved downwardly by a single means and vacuum is applied to them from a single source. Similarly, they are moved upwardly past the smoothing rings and a single pressure source causes discharge of the green containers from the male molds, and the containers are sintered in the same sintering oven. The results are containers suitable for heating analytical (and other) samples of materials, but because they are not made of quartz they do not have the high resistance to heat damage of quartz and therefore aren't suitable for most ashing operations.

EXAMPLE 4

The procedure of Example 1 is repeated but the fibers used are conventional fiberglass fibers, not microfibers. The container made is not really a container but is an extraction thimble, and may be shaped accordingly. It is sintered at a lower temperature, e.g., about 400°-600° C., and is not heat resistant. It may be made of different dimensions from the ashing containers, as may be such containers, too. It is useful as an extraction thimble because it is porous enough to allow passage of the extracting liquid through its walls and bottom, and yet can hold the solid sample being extracted. In the making of this glass container, and in the makings of the microfibrous quartz and borosilicate glass containers, containers of different sizes shapes and materials can be made by utilizing different molds and charges of different fibrous materials (even cellulosic fibers, such as chopped cotton fibers may be used to make green containers or extraction thimbles). However, in all such cases, for best results, it is desirable that the dispersions be what has been characterized herein as dilute.

The invention has been described with respect to various illustrations and working examples thereof but is not to be limited to those because one of skill in the art, after reading the specification, will be able to utilize substitutes and equivalents without departing from the invention.

What is claimed is:

1. A process for manufacturing a container for holding materials which comprises: depositing a dispersion of fibers in a liquid onto an interior wall of a liquid permeable female mold; removing liquid from the deposited dispersion by applying a pressure differential across the mold, with a higher pressure being interior of the mold and a lower pressure being exterior of the mold; moving a liquid permeable male mold into the female mold; terminating the differential pressure across the female mold; applying a pressure differential across the male mold, with a higher pressure being exterior of the mold and a lower pressure being interior of the mold, to press the container onto the male mold; withdrawing the male mold from the female mold, with the container being held to the male mold; and releasing the container from the male mold.

2. A process according to claim 1 wherein the male mold matches the female mold, with the container therein.

3. A process according to claim 1 wherein the pressure differential across the female mold is effected by applying a vacuum exterior to the female mold and the pressure differential across the male mold is effected by applying a vacuum interior of the male mold.

4. A process according to claim 3 wherein the male mold matches the female mold, with the container between said molds, and the dispersion of fibers in the liquid is an aqueous dispersion of quartz fibers, with a weight percentage of said fibers in the dispersion being in a range of 0.2 to 4%.

5. A process according to claim 4 wherein said male and female molds are of microperforated or microporous stainless steel, the quartz fibers are quartz microfibers, the container is of substantially flat cylindrical shape, the container has an exterior thereof smoothed by contact with a smoothing element as it is removed from the female mold with the male mold and the container is sintered to permanent shape after being released from the male mold.

6. A process according to claim 1 wherein the male and female molds are of microperforated or microporous thin material.

7. A process according to claim 1 wherein the container is substantially flat cylindrical in shape, is made of microfibrous quartz, and has an exterior thereof smoothed by contact with a smoothing element as the container is removed from the female mold with the male mold.

8. A process according to claim 1 wherein the dispersion of fibers in liquid is an aqueous dispersion of a material selected from the group consisting of quartz, glass, and a mixture of quartz and glass, with a weight percentage of said fibers in the aqueous dispersion being in a rnage of 0.2 to 4%, and the container is sintered to permanent shape.

* * * * *